US007038016B2

(12) United States Patent
Talarico et al.

(10) Patent No.: US 7,038,016 B2
(45) Date of Patent: May 2, 2006

(54) METHODS FOR PURIFICATION OF AN ACTIVATED PEG SOLUTION AND FOR THE SYNTHESIS OF A MODIFIED HEMOGLOBIN SOLUTION

(75) Inventors: Todd Lewis Talarico, Cary, NC (US); Cyrus John Stacey, Raleigh, NC (US)

(73) Assignee: Apex Bioscience, Inc., Chapel Hill, NC (US)

( * ) Notice: Subject to any disclaimer, the term of this patent is extended or adjusted under 35 U.S.C. 154(b) by 557 days.

(21) Appl. No.: 09/934,300

(22) Filed: Aug. 21, 2001

(65) Prior Publication Data

US 2003/0045602 A1    Mar. 6, 2003

(51) Int. Cl.
*A61K 35/14* (2006.01)
*A61K 38/16* (2006.01)
*A61K 39/385* (2006.01)
*G01N 33/53* (2006.01)
*C07K 1/00* (2006.01)

(52) U.S. Cl. ............... 530/385; 530/402; 530/412; 530/421; 435/962; 514/6; 424/195.11; 525/54.1

(58) Field of Classification Search ............... 530/385, 530/416, 417, 414, 402, 521; 435/20.6, 962; 525/54.1; 424/195.41; 514/6
See application file for complete search history.

(56) References Cited

U.S. PATENT DOCUMENTS

| 4,179,337 | A | * | 12/1979 | Davis et al. ............... 435/181 |
| 4,229,571 | A | * | 10/1980 | Katsunuma ............... 536/18 |
| 4,831,012 | A | | 5/1989 | Estep ............... 514/6 |
| 4,929,354 | A | * | 5/1990 | Meyering et al. ...... 210/321.61 |
| 5,084,558 | A | | 1/1992 | Rausch et al. ............... 530/385 |
| 5,234,903 | A | | 8/1993 | Nho et al. |
| 5,256,559 | A | * | 10/1993 | Maraganore et al. ......... 514/12 |
| 5,439,882 | A | * | 8/1995 | Feola et al. ............... 514/6 |
| 5,464,814 | A | | 11/1995 | Sehgal et al. ............... 514/6 |
| 5,468,478 | A | * | 11/1995 | Saifer et al. ............. 424/78.27 |
| 5,478,738 | A | * | 12/1995 | Goldstein et al. ........... 435/201 |
| 5,741,894 | A | | 4/1998 | Azari et al. ................. 530/385 |
| 5,840,852 | A | | 11/1998 | Rausch et al. ............... 530/385 |
| 5,900,402 | A | * | 5/1999 | Shorr ............... 514/6 |
| 6,017,943 | A | | 1/2000 | Acharya et al. ............. 514/410 |
| 6,150,507 | A | | 11/2000 | Houtchens et al. ......... 530/385 |
| 2004/0067898 | A1 | * | 4/2004 | Somberg et al. ............... 514/29 |

FOREIGN PATENT DOCUMENTS

| JP | 53038617 A | * | 4/1978 |
| WO | WO 90/15613 | | 12/1990 |
| WO | WO 02/44214 A1 | | 6/2002 |

OTHER PUBLICATIONS

Talarico et al. Biochim. Biophys. Acta 1476: 53-65, 2000.*
Zalipsky et al. J. Macromol. Sci. Chem. A21: 839-845, 1984.*
Woghiren et al. Bioconj. Chem. 4: 314-318, 1993.*
Greenwald et al. Bioconjugate Chem. 7: 638-641, 1996.*
Blume et al. Biochim. Biophys. Acta 1029: 91-97, 1990.*
Abuchowski et al. J. Biol. Chem. 252: 3578-3581, 1977.*
Iwashita, Y., et al., "A New Resuscitation Fluid 'Stabilized Hemoglobin' Preparation and Characteristics," *Biomaterials, Artificial Cells, and Artificial Organs*, 1988, pp. 271-280, vol. 16(1-3), Marcel Dekker, Inc.
Iwashita, Y., et al., "Relationship Between Chemical Properties and Biological Properties of Pyridoxalated Hemoglobin-Polyoxyethylene," *Biomaterials, Artificial Cells, and Artificial Organs*, 1992, pp. 299-307, vol. 20(2-4), Marcel Dekker, Inc.
Sakai, H., et al., "Surface Modification of Hemoglobin Vesicles with Poly(ethyleneglycol) and Effects on Aggregation, Viscosity, and Blood Flow During 90% Exchange Transfusion in Anesthetized Rats," *Bioconjugate Chemistry*, 1997, pp. 23-30, vol. 8, American Chemical Society, USA.
Sakai, H., et al., "Synthesis and Physiocochemical Characterization of a Series of Hemoglobin-Based Oxygen Carriers: Objective Comparison Between Cellular and Acellular Types," *Bioconjugate Chemistry*, 2000, pp. 56-64, vol. 11, American Chemical Society, USA.
Miles, P., et al., "Detection of Residual Polyethylene Glycol Derivatives in Pyridoxylated-Hemoglobin-Polyoxyethylene Conjugate," *Artificial Cells, Blood Substitutes, and Immobilization Biotechnology*, 1997, pp. 315-326, vol. 25(3), Marcel Dekker, Inc., USA.
Privalle, C., et al., "Pyridoxalated Hemoglobin Polyoxyethlene: a Nitric Scavenger with Antioxidant Activity for the Treatment of Nitric Oxide-Induced Shock," *Free Radical Biology & Medicine*, 2000, pp. 1507-1517, vol. 28 (10), Elsevier Science, Inc. USA.
Talarico, T., et al., "Autoxidation of Pyridoxalated Hemoglobin Polyoxyethylene Conjugate," *Biochemical and Biophysical Research Communications*, 1998, pp. 354-358, vol. 250(2), Academic Press, USA.
Matsumura, S., "Large Scale Production and Characterization of Lyophilized Pyridoxalated Hemoglobin-Polyoxyethylene (PHP)," *Biomat., Art. Cells & Immob. Biotech.*, 1992, vol. 20(2-4), pp. 435-438.
Talarico, T.L., "Comparability Analysis to Support a Manufacturing Site Change and Process Modifications for a Biopharmaceutical: A Regulatory Submission Case Study," *BioPharm*, 1999, vol. 12(1), pp. 42-47.

* cited by examiner

*Primary Examiner*—S. Devi
(74) *Attorney, Agent, or Firm*—Alston & Bird LLP

(57) ABSTRACT

The present invention employs a dissolved activated polyethylene glycol (aPEG) or related molecule that has been passed through a filtration means for the substantial reduction of bioburden or endotoxin levels in the aPEG solution. The resulting filtered aPEG solution can be used for the preparation of a PEGylated hemoglobin solution containing substantially reduced levels of bioburden or endotoxin.

8 Claims, 5 Drawing Sheets

METHODS FOR PURIFICATION OF AN ACTIVATED PEG SOLUTION AND FOR THE SYNTHESIS OF A MODIFIED HEMOGLOBIN SOLUTION

FIELD OF THE INVENTION

The invention relates to methods for the purification of an activated polyethylene glycol solution and for the synthesis of a modified hemoglobin solution.

BACKGROUND OF THE INVENTION

Blood is the circulating liquid that transports oxygen and nutritive materials to the tissues of the body and removes carbon dioxide and other metabolic products and wastes for excretion. Blood consists of a fluid, plasma, in which a variety of components including red blood cells are suspended. Stedman's Medical Dictionary, $26^{th}$ edition, page 214 (1995). A particularly prevalent component of red blood cells is the protein hemoglobin, which is specifically responsible for the transport of oxygen from the lungs to other tissues in the body.

Because of the great demand for blood in the United States and throughout the world, intense research efforts have been directed towards the development of hemoglobin-based blood substitutes. Such substitutes have been produced with a variety of modifications of purified hemoglobin in order to prevent toxicity or otherwise enhance the properties of the molecule, with one particularly important class of modification accomplished using molecules of the polyethylene glycol (PEG) family that have been activated (aPEGs) so as to be capable of chemically modifying proteins. Such PEGylation is important because it favorably alters the activity, solubility, circulating half-life in vivo, toxicity and immunogenicity of hemoglobins. See, generally, Delgado et al. (1992) Crit. Rev. Ther. Drug Carrier Sys. 9:249–304; Greenwald et al. (2000) Crit. Rev. Ther. Drug Carrier Sys. 17: 101–161.

The literature reveals that hemoglobin has been PEGylated using a variety of aPEG compounds. One aPEG used to modify hemoglobin is the activated PEG molecule polyoxyethylene ($\alpha$-carboxymethyl, $\omega$-carboxymethoxypolyoxyethylene) (POE), which is reacted with pyridoxylated hemoglobin to obtain pyridoxylated hemoglobin polyoxyethylene (PHP). Talarico et al. (1999) Biochem. et Biophys. Acta 1476:53–65, herein incorporated by reference. POE-modified hemoglobins are of particular interest because they contain cellular proteins that enhance their functionality as scavengers of nitric oxide (NO), a compound implicated in a variety of diseases. Thus there is great potential use of such PHPs as therapeutic agents for the treatment of diseases linked to the presence of excess NO including, for example, systemic inflammatory response syndrome (SIRS), a critical medical illness which is recalcitrant to existing therapies. Privalle et al. (2000) Free Radic. Biol. Med. 28:1507–17, herein incorporated by reference.

Although PHP and other PEGylated hemoglobins have great promise in these and other therapeutic applications, there are a number of problems affecting such uses, notably the presence of contaminating compounds that affect their safety or efficacy. Dangerous viruses such as the HIV/AIDS virus or hepatitis viruses, for example, often contaminate the whole blood used to prepare the hemoglobin fraction used in PEGylation, and must be removed at some point during preparation of the final PEGylated product by filtration or other means. Additionally, bioburden such as bacteria can be a source of contamination of either the hemoglobin or raw materials such as an aPEG, as can endotoxins, the complex cell-wall lipopolysaccharide (LPS) macromolecules of gram-negative bacteria that can cause fever, diarrhea, hemorrhagic shock, and other tissue damage. Stedman's Medical Dictionary, $26^{th}$ edition, page 572 (1995).

Bioburden and endotoxins are a particularly problematic source of contamination because of the lack of adequate methods for removing them from the aPEG raw material used in PEGylation. As discussed previously, aPEG molecules are activated molecules of the polyethylene glycol family. Many such activated molecules are labile in water, and as a result are typically added to the hemoglobin fraction in a powdered form, rather than in solution. Although aPEGs in this form are relatively stable, as powders they cannot be processed for the removal of contaminants using the methods available for dissolved aPEGs, such as filtration techniques. Although these contaminants can be removed post-PEGylation, such removal has undesirable consequences. For example, while endotoxins can be removed from PHP by chromatography, such chromatography results in undesirable changes to the protein composition of the PHP.

Thus there is a long-felt need for a method of purifying aPEGs for use with peptide molecules and polypeptides such as hemoglobin. Furthermore, there is a long-felt need for methods of using such purified dissolved aPEGs in the PEGylation of peptides and polypeptides such as hemoglobin, wherein the solvent in which the aPEG is dissolved does not result in the substantial denaturation or degradation of the pepetide or polypeptide such as hemoglobin.

SUMMARY OF THE INVENTION

The present invention provides methods for the preparation of an activated PEG (aPEG) and PEGylated hemoglobins. Specifically, the present invention provides a method of preparing a purified aPEG solution that is stabile and substantially free of contaminants. The method comprises dissolving an aPEG in a solvent in which the aPEG is stabile and filtering the dissolved aPEG through a filtration means which substantially reduces the levels of contaminants in the resulting filtered aPEG solution. In one embodiment of the present invention the aPEG used is POE.

The present invention also provides a method of preparing a PEGylated hemoglobin solution that is substantially free of contaminants. The method comprises dissolving an aPEG in a solvent suitable for addition to a hemoglobin solution and in which the aPEG is stabile, filtering the dissolved aPEG through a filtration means which substantially reduces the levels of contaminants in the resulting filtered aPEG solution, and combining the resulting filtered aPEG solution with a hemoglobin solution in a combining means. In one embodiment of the present invention the aPEG used is POE.

DETAILED DESCRIPTION OF THE INVENTION

Figure 1:
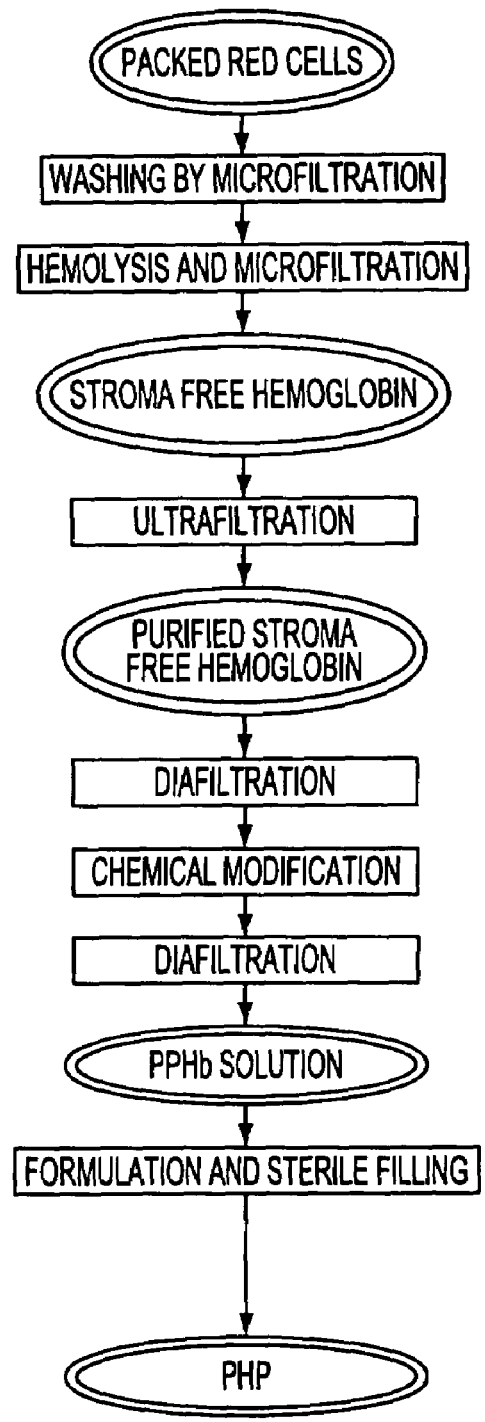
FIG. 1 is a schematic overview of PHP synthesis.

The methods of the present invention relate to the preparation of an aPEG solution that is substantially free of contaminants, and to methods for using these purified aPEGs in the preparation of a PEGylated hemoglobin solution. More specifically, the methods of the present invention provide for the preparation of a filtered aPEG solution that is stabile and substantially free of contaminants. The methods involve dissolving an aPEG in a solvent in which the aPEG is stabile and then filtering the dissolved aPEG through a filtration means which substantially reduces the levels of contaminants in the resulting filtered aPEG solution.

"aPEG" and the plural "aPEGs" refer to polyethylene glycol (PEG) and molecules related to PEG that have been activated so as to be capable of chemically modifying proteins, peptides, or other molecules. Generally, an aPEG has a molecular weight of about 3 kD to about 50 kD. "aPEG" is contemplated to encompass a variety of such compounds including, but not limited to, activated polyethylene glycol, activated polypropylene glycol, and modifications and derivatives thereof such as POE, amine PEGs, maleimide PEGs, succinimimidyl PEGs, succinimidyl succinate PEGs, and base PEGs. Other examples of aPEGs are provided in Greenwald et al. (2000) *Crit. Rev. Ther. Drug Carrier Sys.* 17: 101–161, and Delgado et al. (1992) *Crit. Rev. Ther. Drug Carrier Sys.* 9:249–304, both of which are herein incorporated by reference.

The purified aPEGs of the invention can be used to PEGylate any peptide or protein of interest. As used herein, "PEGylate" or "PEGylation" refer to the chemical modification of a peptide, polypeptide, or other molecule by an aPEG. In a preferred embodiment, the protein of interest is hemoglobin. However the invention is intended to apply generally to any protein, peptide or other molecule that is to be PEGylated. Such proteins and peptides include, for example, growth hormone, growth factors such as FGF, IGF, IL-2, VEGF, etc. Further examples of such proteins and peptides are provided in, for example, Greenwald et al. (2000) *Crit. Rev. Ther. Drug Carrier Sys.* 17: 101–161, and Delgado et al. (1992) *Crit. Rev. Ther. Drug Carrier Sys.* 9:249–304. In a preferred embodiment, PEGylation is of hemoglobin with POE.

In the purification method, an aPEG of interest is dissolved in a solvent in which it is stabile. As used herein, the term "stabile" is intended to mean that a high percentage of an aPEG remains in its active form during the duration of the PEGylation. By "high percentage" is intended a value of more than about 80%, 85%, 90%, 91%, 92%, 93%, 94%, 95%, 96%, 97%, 98%, 99% or greater.

Stability can be measured in a variety of ways known to one of skill in the art, including methods of assaying the loss of the activating group of the aPEG over time.

For example, the stability of POE in solution may be monitored by determining the amount of N-hydroxysuccinimide (NHS) loss from POE occurring over time. The amount of NHS loss can be determined by high performance liquid chromatography (HPLC). POE species can be separated and quantitated using this method and a rate of NHS loss may be determined. This can be stated as the percent of activity remaining over the course of exposure to a solvent. Alternatively, the aPEG can be derivatized and the different forms can be separated by HPLC directly. An example of such a method for determining the stability of POE in solution is given in Example 3 of the experimental section. Although this is a preferred method for such a determination, other such methods are known to the skilled artisan.

A number of solvents can be used in the practice of the invention, including, but not limited to, ethanol, methanol, acetonitrile, dimethylsulfoxide, and tetrahydrofuran. The solvent is chosen to maintain the stability of the aPEG. A number of factors will be considered in choosing a solvent including solubility of the aPEG in the solvent, stability of the aPEG in the solvent, compatibility of the solvent with the protein of interest if the aPEG will be used with a particular protein, toxicity of the solvent, miscibility of the solvent with water, and the ability of the production process to remove the solvent.

Once an aPEG has been dissolved in a solvent in which it is stabile, it is purified through a filtration means. As defined herein, "filtration means" refers to a means for substantially reducing the levels of contaminants in the dissolved aPEG by filtration. The present invention contemplates a variety of differently formulated filtration means targeted at different contaminants that must be reduced to differing degrees, with the particular character of the filtration means varying depending upon the contaminant to be reduced. As defined herein, "contaminants" refers to compounds including, but not limited to, bioburden, endotoxin, and particulates.

In one embodiment of the present invention, the filtration means is targeted to the substantial reduction of contaminants including bioburden and endotoxin. "Bioburden," as defined herein, refers to organisms such as bacteria that may be present in the dissolved aPEG. There are a variety of filtration means known to one of ordinary skill that can be used to remove bioburden, including filtration membranes with a pore size sufficiently small so as to retain bioburden while allowing dissolved aPEG to pass into the filtrate. Such membranes include, for example, 0.2 μm sterilization filters. The choice of a particular sterilization filter depends upon a variety of factors including the solvent in which the aPEG has been dissolved. Specifically, extremely non-polar solvents may damage or degrade particular filters. Thus an aPEG dissolved in a polar solvent may be filtered using a filter composed of polyether sulfone or cellulose acetate, such as a Sartobran® filter (Sartorius), whereas an aPEG dissolved in an extremely non-polar solvent may be appropriately filtered using a filter composed of polytetrafluoroethylene (PTFE) or nylon. For example, for moderately polar solvents such as methanol, ethanol, and isopropanol, $N_{66}$® Posidyne® (Pall corporation) or Durapore® (Millipore) filters are contemplated, whereas Sartoflour® (Sartorius) or Emflon PFR® (Pall corporation) filters are contemplated for very non-polar solvents.

"Endotoxin," as defined herein, refers to the complex cell-wall lipopolysaccharides of gram-negative bacteria. Endotoxins are capable of producing a number of serious medical conditions including, for example, septic shock, where symptoms range from minor effects such as chills, fever, and nausea, to serious conditions such as heart failure, coma and, in the most extreme cases, death, and are one of the most prevalent forms of exogenous pyrogens, that is, fever-inducing compounds. *Stedman's Medical Dictionary*, $26^{th}$ edition, page 1475 (1995). Endotoxin levels can be substantially reduced by a variety of filtration means, including filtration means where negatively-charged endotoxins are retained by a positively-charged filtration means. One example of a positively-charged filtration means capable of removing endotoxin is the filtration membrane $N_{66}$® Posidyne® (Pall corporation). Other membranes such as the Zeta Plus® Series (Cuno) and the Sartobind™ Membrane Absorbers (Sartorius) may also be used, as can positively-charged adsorbents including, for example, positively-charged resins and packed columns. The choice of a particular solvent, buffer, salt condition, etc, for each of these filtration means would be well known to the skilled artisan.

Filtration through the filtration means will result in an aPEG solution that is substantially reduced in bioburden or endotoxin. By "substantially reduced" is intended that the contaminants are reduced by at least about 60%, 65%, 70%, 75%, 80%, 85%, 90%, 91%, 92%, 93%, 94%, 95%, 96%, 97%, 98%, 99% or greater, with the intended value depending upon the particular contaminant being substantially reduced. Substantial reduction of bioburden contaminants, for example, refers to reductions of bacterial bioburden to not more than 1 colony forming units per ml (CFU/ml), and is preferentially directed to 0 CFU/ml. Determination of bacterial bioburden can be assayed by a variety of methods well known to those of ordinary skill including, but not limited to, capturing organisms on filters, placing the filters on R2A agar plates at 30–35° C. for 4 days, and then counting the number of resulting colonies. See, for example, *Official Methods of Analysis of AOAC International* (1995) 17$^{th}$ ed., 17.2.05 Official Method 986.32 or 17.3.08 Official Method 983.25. Alternatively, bioburden can be assayed by techniques such as direct plating or by pour plating, both of which are known to the skilled artisan. Substantial reduction of endotoxin contaminants refers to reductions of endotoxin levels by 500 and more preferentially >5000 EU/cm$^2$ of filter area. Determination of endotoxin levels can be assayed by a variety of methods well known to those of ordinary skill including, but not limited to, the Limulus Amoebocytic Lysate (LAL) assay. USP 24, NF19 <85> *Bacterial Endotoxins Test,* 1829–1831.

Furthermore, an aPEG solution that has been substantially reduced in contaminants is characterized by not inducing pathophysiological effects characteristic of the presence of contaminants upon in vivo administration to a subject (i.e. a mammal, preferably a rabbit, mouse, bovine, pig, monkey, human, etc.). For instance, physiological symptoms include fever, disseminated intravascular coagulation, hypotension, and cardiovascular shock. Roth and Levin (1994) *Meth. Enzymol.* 231:75–91. Hence, as used herein, an aPEG solution "substantially reduced" in contaminants is one that is noninfectious, such that the solution can be manipulated without harming or infecting anyone exposed thereto.

"Filtration means" may be used to refer to a single filtration means, that is, to a single membrane, or other means of filtration. However, the present invention is not limited to a single such means of filtration, and instead encompasses both single and multiple filtration means. Thus, "filtration means" is used to encompass multiple filtration methods. Multiple filtration means may find particular utility in situations where, for example, it is advantageous to remove bioburden on one membrane and endotoxin on a separate membrane, packed column, impregnated media, etc. One of ordinary skill in the art will be able to determine situations where such multiple filtration means are preferable. Such situations may include instances where successive filtration means act to reduce bioburden or endotoxin levels below those achieved by a single filtration means, and instances where no single filtration means exhibits all the advantageous properties that two filtration means used together exhibit. One example of such multiple filtration means includes a combination of sterilizing filter to remove bioburden and positively charged impregnated depth filter to remove endotoxins.

In addition to the methods presented above for the preparation of a filtered aPEG solution that is stabile and substantially free of contaminants, the present invention also provides a method for using these purified aPEGs in the preparation of a PEGylated peptide or polypeptide solution. Specifically, the present invention provides a method of dissolving an aPEG in a solvent suitable for addition to a peptide or polypeptide solution and in which the aPEG is stabile, filtering the dissolved aPEG through a filtration means which substantially reduces the levels of contaminants in the resulting filtered aPEG solution, and combining the resulting filtered aPEG solution with a peptide or polypeptide solution in a combining means.

In a preferred embodiment, the present invention is directed to a method of using a purified aPEG in the preparation of a PEGylated hemoglobin solution. Specifically, the present invention provides a method of dissolving an aPEG in a solvent suitable for addition to a hemoglobin solution and in which the aPEG is stabile, filtering the dissolved aPEG through a filtration means which substantially reduces the levels of contaminants in the resulting filtered aPEG solution, and combining the resulting filtered aPEG solution with a hemoglobin solution in a combining means.

As defined herein, "hemoglobin solution" refers to any of the various forms of hemoglobin solutions obtained from whole blood or recombinant means that can be used for PEGylation. Such solutions may contain other macromolecules in addition to hemoglobin. It is often desirable, for example, that hemoglobin solutions that are PEGylated to produce PHP also contain important endogenous antioxidant molecules such as catalase and SOD. Privalle et al. (2000) *Free Radic. Biol. Med.* 28:1507–17. The preferred blood used in the invention is outdated human blood. However, all the methods of the present invention can be used with bovine, porcine, ovine and other mammalian blood with only minor modifications which are known to a skilled artisan. Although the present invention specifically contemplates the use of hemoglobin solutions prepared for modification with POE, other aPEG modifiers are contemplated.

The term "solvent suitable for addition to a peptide or polypeptide solution," as defined herein, refers to a solvent which, when added to the peptide or polypeptide solution in the required proportion, does not significantly denature or degrade the peptide or polypeptide in the solution during the duration of the PEGylation reaction. As used herein, peptides or polypeptides are not significantly denatured or degraded if the levels of these compounds remain more than about 90%, 91%, 92%, 93%, 94%, 95%, 96%, 97%, 98%, 99% or greater undegraded or undenatured after the addition of the solvent for the duration of the PEGylation.

As used herein, "solvent suitable for addition to a hemoglobin solution" is used to refer to a specific embodiment of the present invention in which the polypeptide is hemoglobin. The definition of this term is identical to that defined above for solvents suitable for addition to a peptide or polypeptide solution. That is, a solvent suitable for addition to a "hemoglobin solution" is one does not significantly degrade hemoglobin during the course of the reaction. Hemoglobin is not significantly denatured or degraded if the levels of hemoglobin remains more than about 90%, 91%, 92%, 93%, 94%, 95%, 96%, 97%, 98%, 99% or greater undegraded or undenatured after the addition of the solvent for the duration of the PEGylation.

There are a variety of assays known to the skilled artisan for measuring degradation of a peptide or polypeptide. Degradation for polypeptides and peptides in general can be assayed by techniques including, for example total soluble protein, UV-VIS spectra, enzymatic activity, etc. Degradation for the polypeptide hemoglobin can be assayed by these methods, and also by methods specific to hemoglobin, such as a hemoglobin concentration or methemoglobin assay.

The choice of a solvent suitable for addition to a peptide or polypeptide solution will depend upon a variety of factors. For example, the choice of the solvent requires a balancing of the solubility and stability of the dissolved aPEG with the negative effects the solvent has on the peptide or polypeptide solution. It may be necessary to determine the fraction of the PEGylation reaction volume that can be occupied by the solvent without denaturing or degrading the peptide or polypeptide solution. Thus, for example, a particular solvent may be appropriate for use when it is added at lower concentrations, up to, for example, 15% of the final reaction volume, while higher proportions of the same solvent may result in denaturation or degradation of the peptide or polypeptide solution. Thus, a range of factors will need to be considered when determining the choice of a particular suitable solvent including, but not limited to, the solubility of the aPEG in the solvent, the stability of the aPEG in the solvent, the effects of the solvent on the peptide or polypeptide solution, and the maximum proportion of the PEGylation reaction volume that the solvent can occupy with no deleterious effects.

Addition of organic solvents to aqueous protein solutions may result in substantial protein denaturation as evidenced by a loss of a protein's activity or by protein aggregation and precipitation. Thus use of specific solvents, their concentration and contact time will vary for each peptide or polypeptide to be modified by PEGylation.

For addition to a hemoglobin solution, methanol, ethanol, and acetonitrile can be used. For use with POE in hemoglobin modification, ethanol may be preferred. With ethanol, even at 20% of the final volume no substantial denaturation or degradation of the hemoglobin solution was exhibited.

As defined herein, "combining means" refers to an apparatus for mixing dissolved aPEG and a peptide or polypeptide solution and includes any device for mixing two solutions, including, but not limited to, devices for mixing small amounts of two solutions as well as devices for carrying out such mixings at process scales. Because it is desirable to exclude as much externally-introduced contamination as possible from the aPEG and peptide or polypeptide fractions of the PEGylation reaction, one particularly desirable combining means is an apparatus which allows for the aseptic introduction of the aPEG and peptide or polypeptide fractions. In one particular embodiment, this apparatus may have several inlet ports through which these fractions can be aseptically introduced. Such aseptic introduction is contemplated to occur by a variety of mechanisms, including by aseptically coupling the filtration means for filtering an aPEG to an inlet port of the apparatus through a length of tubing of a type known to one of ordinary skill.

As an example, aseptic coupling can be accomplished by performing the operations in an area of appropriate classification. Alternatively, the vessel can be coupled to a pre-sterilized filter containing a valve and sanitary filter. The valve can be closed and the vessel and connector can be sterilized via steam introduction. At the time of processing, the valve is opened and the path-length from the outlet of the filter to the vessel is sterile.

The method of the present invention for the preparation of a PEGylated hemoglobin solution using dissolved aPEG offers a number of advantages over conventional methods that utilize an aPEG in powdered form. One particularly important advantage is the higher sterility resulting when closed fluid delivery connections are used. Such introduction can be accomplished by, for example, aseptically coupling the aPEG filtration means to the combining means. This is in contrast to the situation for the addition of powdered aPEG, where bioburden introduction must be controlled by, for example, adding powdered material to an opened port of the combining means under a laminar-flow hood, or where personnel are gloved and trained on the proper methods of making such connections but no special environment is used.

Additionally, advantages result from the use of dissolved aPEGs as compared to aPEGs in powdered form. One such advantage is the decrease in high molecular weight product formation in process-scale PEGylation reactions using dissolved aPEGs as opposed to aPEG powders. Although such products are not formed to any substantially different extent in small-scale reactions using dissolved aPEG than in similar reactions using aPEG in powdered form, substantially smaller amounts of such reaction products are formed in process-scale reactions using dissolved aPEG only. As defined herein, "small-scale" reactions refer to reactions of 1–5 liters, whereas reactions of 10 liters or more are termed "process-scale." "Substantially smaller amounts," as defined in the context of these high molecular weight reaction products is contemplated to mean reduced by at least 40%, 50%, 60%, 70%, 80%, 85%, 90%, 91%, 92%, 93%, 94%, 95%, 96%, 97%, 98%, 99% or greater. Methods for the determination of levels of such materials include the use of size-exclusion chromatography (SEC), as described in Talarico et al., (1999) *Biochemica et Biophysica Acta* 1476: 53–65, or other methods such as low angle laser light scattering, particulate measurements, and direct counting.

In particular, the use of dissolved aPEG in process-scale PEGylation results in the reduction in high molecular weight products in process-scale production of PHP using POE. SEC analyses of PHP obtained using powdered POE shows the presence of a high mass peak of about 15,548,068. In stark contrast, SEC analysis of process-scale reactions performed with dissolved POE shows substantially smaller amounts of this high molecular weight peak. As one specific exemplar of this effect, PHP produced from POE dissolved in 95% ethanol shows essentially no such high molecular weight material, at least in the sensitivity range of the analysis performed.

In addition, the introduction of POE as a solution results in a reduction of macroscopic particulates. For example, POE added as a powder to large reaction vessels results in a condition where a significant amount of the powder rests on the liquid surface until it can dissolve. If large particles or granules of POE are present, the protein in the solution (hemoglobin) is reacted on the granule surface. Since the POE is bifunctional, crosslinking of the protein results. The crosslinking is extensive at the granule surface and a protein "gel" results. This gel, or cross-linked protein mass, is 1 or more microns in diameter. Formation of these macroparticulates results in the plugging of filters used in downstream purification operations and in a loss of product. By eliminating any "granules" of POE present in powdered addition, the formation of these cross-linked protein particles is eliminated. The result is a more efficient and reproducible chemical modification reaction and purification process.

In the following section, illustrative examples will be presented. These examples are presented to illustrate a best mode and preferred embodiments of the present invention, and are not meant to limit the claimed invention unless otherwise specified.

EXPERIMENTAL

Example 1

Assay of Bioburden Reduction in a Filtered POE Solution 100,7 grams of 3000 MW POE were dissolved in 300 ml of 95% ethanol and 240 ml of the resulting solution were filtered through a 47 mm diameter, 0.2 μm Posidyne® filter under positive pressure. The filtrate was collected in a sterile glass jar and samples were removed, diluted, and filtered through a Milliflex® filter unit for enumeration of bioburden. The samples were plated on sterile R2A agar and incubated for 4 days at 30–35° C. See, for example, *Official Methods of Analysis of AOAC International* (1995) 17$^{th}$ ed., 17.2.05 Official Method 986.32 or 17.3.08 Official Method 983.25. The POE solution contained 151 CFU/ml prior to filtration and 0 CFU/ml after filtration.

Example 2

A. Assay of Endotoxln Reduction in a Filtered POE/Ethanol Solution 1 ml of purified *E. coli* LPS endotoxin (Charles Rivera Endosafe®) was added to 435 ml of a 3000 MW POE/ethanol (1:3 w/v) solution, the solution was sampled and then passed through a 47 mm diameter, 0.2 μm Posidyne® filter under positive pressure and collected into a pyrogen-free glass bottle. The filtrate was sampled and both the starting pool and filtrate pool samples were diluted into endotoxin-free water. The endotoxin content of each dilution was determined by a kinetic turbidimetric LAb assay. The spliced starting pool contained 1,009,200 EU and the filtrate contained 346,375 EU. Thus 662,825 EU were removed by the filter.

B. Assay of Endotoxin Reduction in a Filtered POE/Methanol Solution

Approximately 2 million units of purified *E. coli* LPS endotoxin was added to 12 ml of a 3000 MW POE/methanol (1:3 w/v) solution, the solution was sampled and 10 ml were passed through a 47 mm diameter, 0.2 μm, Posidyne® filter under positive pressure and collected into a pyrogen-free glass bottle. The filtrate was sampled and both the starting pool and filtrate pool samples were diluted into endotoxin-free water. The starting pool contained 1,197,490 EU and the filtrate contained 5290 EU. Thus 1,192,200 EU were removed by the filter.

C. Assay of Endotoxin Reduction in a Filtered POE/Acetonitrile Solution

Approximately 2 million units of purified *E. coli* LPS endotoxin was added to 12 ml of a 3000 MW POE/acetonitrile (1:3 w/v) solution, the solution was sampled and 10 ml were passed through a 47 mm diameter, 0.2 μm Posidyne® filter under positive pressure and collected into a pyrogen-free glass bottle. The filtrate was sampled and both the starting pool and filtrate pool samples were diluted into endotoxin-free water. The starting pool contained 1,095,580 EU and the filtrate contained 273 EU. Thus a reduction of 1,095,307 EU was achieved by the filter.

Example 3

Stability of POE in Ethanol

POE was dissolved in ethanol (1:3 w/v) and aliquoted into a glass vial. At various timepoints an aliquot was removed from the vial and the POE was reacted with ammonium hypoxide. Samples from each timepoint were diluted to 1 mg/ml and analyzed by HPLC to determine the percent activity of the POE in solution. The results are shown below in Table 1.

TABLE 1

Stability of POE in Ethanol

| Time (hr) | Activity (%) |
|---|---|
| 0 | 97.6 |
| 0.5 | 97.6 |
| 1 | 97.3 |
| 2 | 96.8 |
| 3 | 96.0 |
| 4 | 95.8 |
| 24 | 85.9 |

Example 4

Reduction of Endotoxins and High Molecular Weight Products in Process-Scale Preparations of PHP with Powdered POE Versus a Filtered POE/Ethanol Solution A. Preparation of PHP with Powdered POE PHP was prepared from purified stroma-free hemoglobin. The hemoglobin was chemically modified with pyridoxal-5-phosphate under pre-determined conditions. The attachment of POE was performed as follows. First, POE was added to the hemoglobin solution in approximately 10-fold molar excess. For example, 1953 g of POE were added to 70 liters of pyridoxylated hemoglobin contained in a 100 liter stainless steel stirred reactor by pouring the POE through a 4-inch funnel attached to a 1.5-inch sanitary port on top of the reactor. The solution was stirred to allow for dissolution and thorough mixing of the POE. The reaction is allowed to proceed for 40 minutes, and then the modified hemoglobin was removed for further processing.

B. Preparation of PHP with a Filtered POE/Ethanol Solution

PHP prepared from a filtered POE/EtOH solution is manufactured as described above with the following modifications. 1953 g POE was dissolved in 6 liters of 95% ethanol, warmed to 40° C. in a stainless steel, pressure rated vessel, with stirring over 20 minutes. The solution was then filtered under pressure (30 PSIG) through an attached Posidyne® 0.2 μm capsule filter into a 100 liter chemical modification vessel containing pyridoxylated hemoglobin. The solution in the reactor was stirred during the addition of the filtered POE.

C. Endotoxin Reduction in PHP Prepared with Powdered POE Versus a Filtered POE/Ethanol Solution Endotoxins were assayed in PHP prepared either with powdered POE or with a filtered POE/ethanol solution by the LAL gel clot method. See U.S. Pat. No. 24, NF 19 <85>

Bacterial Endotoxins Test, 1829–1831. As is shown in Tables 2 and 3 below, endotoxin levels were substantially reduced when the filtered POE/ethanol solution was used as the feedstock for the chemical modification.

TABLE 2

Endotoxin Content of PHP - Powdered POE Addition

| Lot | Endotoxin Content (EU/ml) |
|---|---|
| A | 0.50 |
| B | 0.26 |
| C | 0.24 |
| D | 0.26 |

TABLE 3

Endotoxin Content of PHP - Liquid POE Addition

| Lot | Endotoxin Content (EU/ml) |
|---|---|
| E | ≦0.03 |
| F | ≦0.03 |
| G | ≦0.03 |
| H | ≦0.06 |

Figure 2:
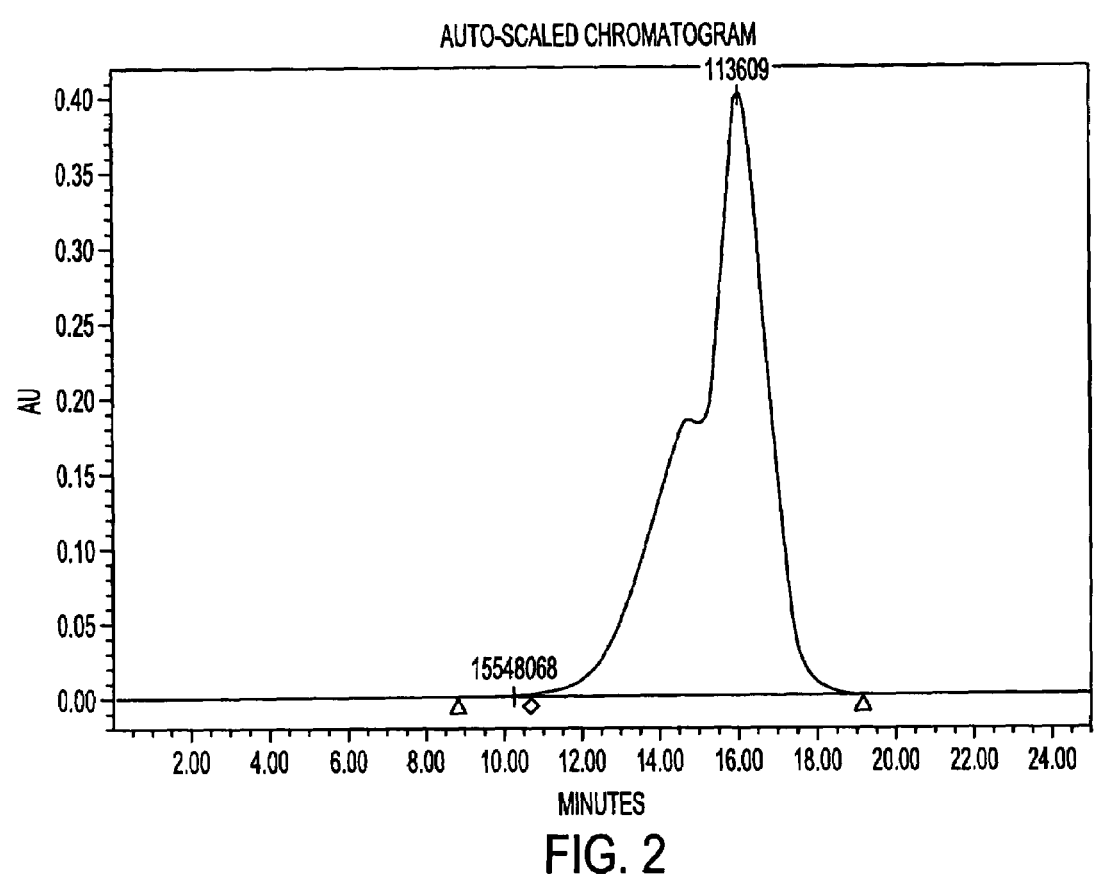
FIG. 2 shows the elution profile of a final formulation of PHP prepared with powdered POE as determined by size exclusion chromatography (SEC).
Figure 3:
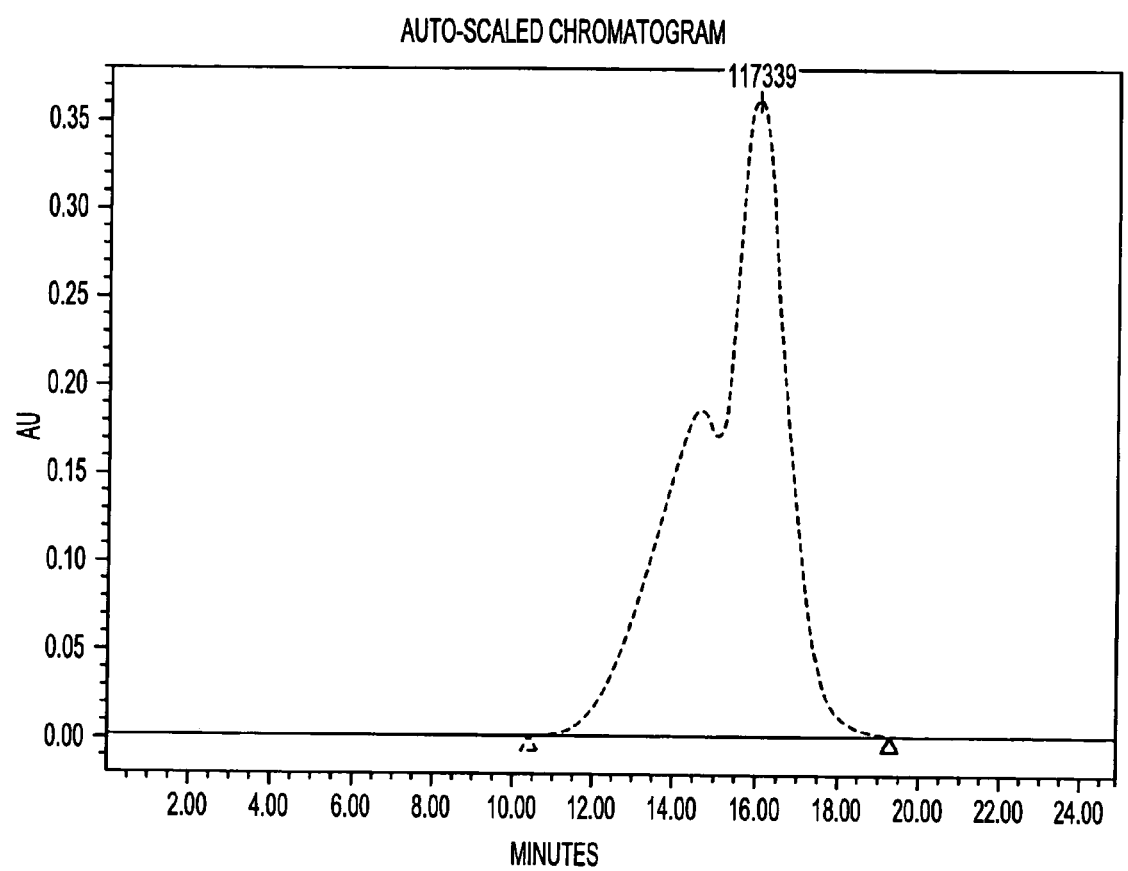
FIG. 3 shows the elution profile of a final formulation of PHP prepared with filtered POE/ethanol solution as determined by SEC.
Figure 4:
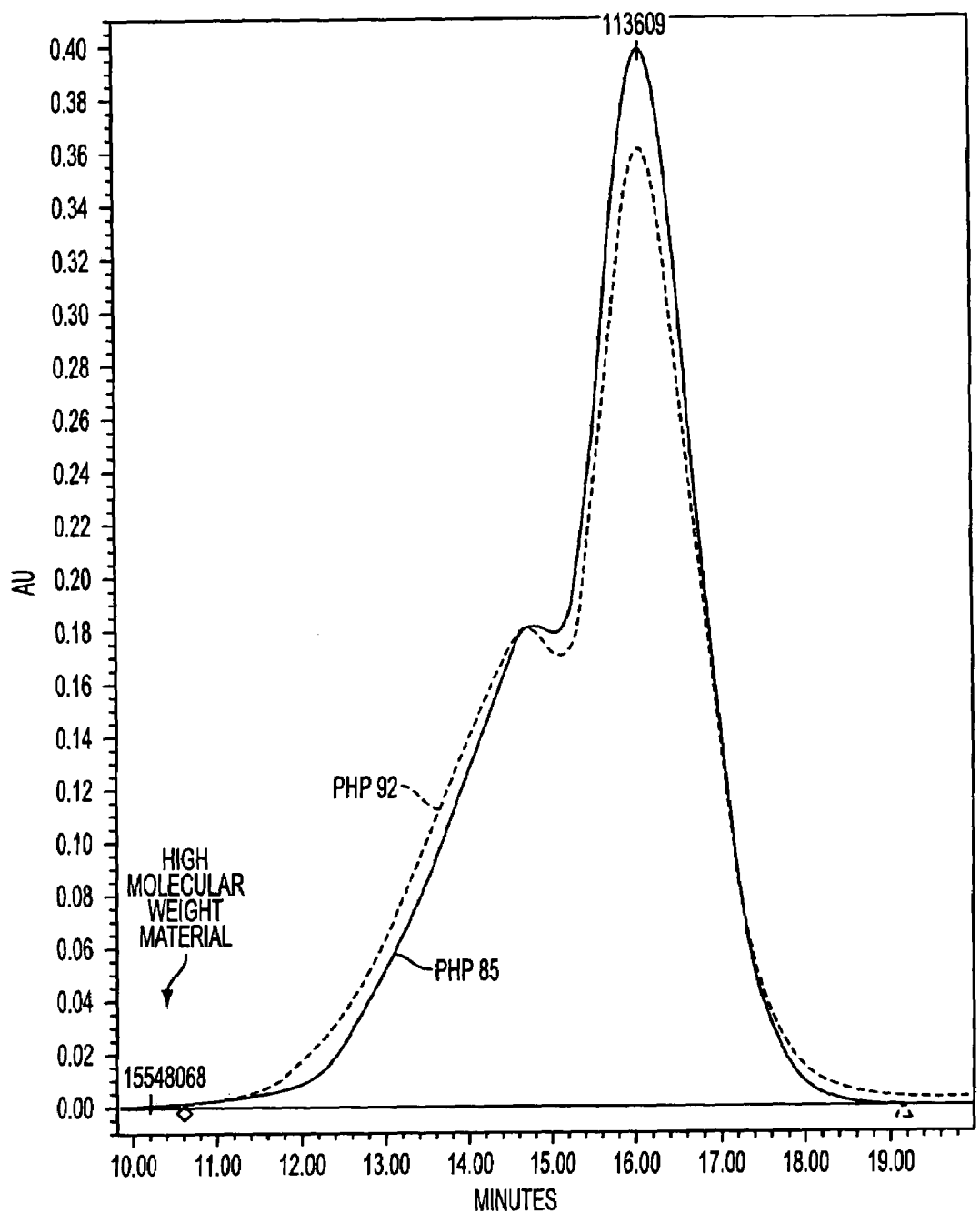
FIG. 4 shows an overlay of the profiles of FIGS. 2 and 3 at a sensitivity of approximately twice that shown in FIGS. 2 and 3.
Figure 5:
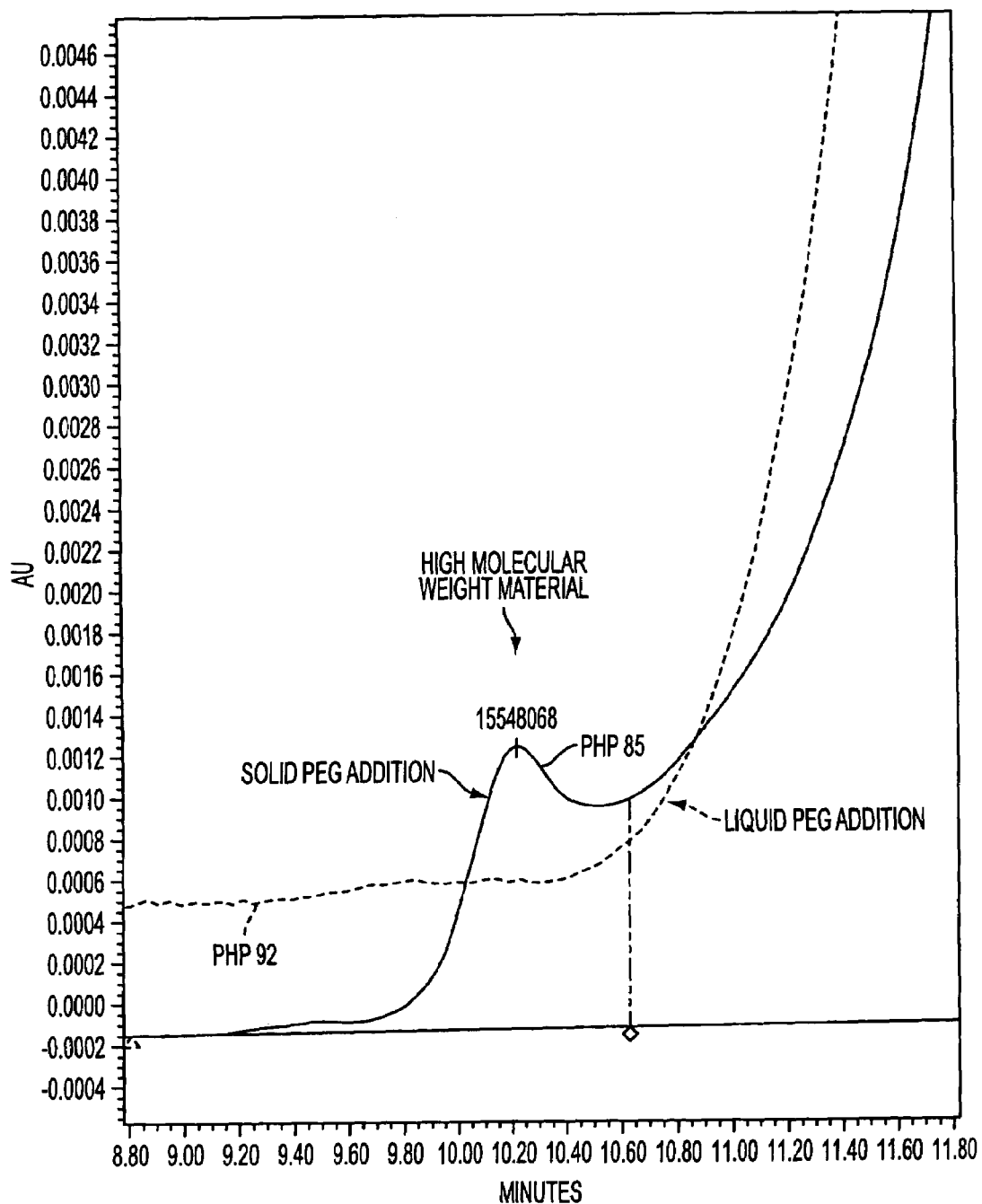
FIG. 5 shows the data of FIG. 4, confined to the vicinity of the high molecular weight fraction of the SEC elution profile and at a sensitivity of approximately 100 times that of FIG. 4.

D. High Molecular Weight Product Reduction in PHP Prepared with Powdered Versus a Filtered POE/Ethanol Solution High molecular weight products were assayed in PHP prepared either with powdered POE or with a filtered POE/ethanol solution. Analyses were performed using SEC as described in Talarico et al., (1999) *Biochemica et Biophysica Acta* 1476:53–65, and are shown in FIGS. 2–5. FIGS. 2 and 3 show the elution profiles of PHP prepared with powdered POE or with filtered POE/ethanol solution respectively. FIG. 4 shows an overlay of the two profiles of FIGS. 2 and 3 at an expanded vertical sensitivity scale of approximately twice that shown for the non-overlaid profiles. FIG. 5 shows the same overlay as that of FIG. 4, but with a vertical sensitivity approximately 100 times that of FIG. 4.

As is shown most clearly in FIG. 5, the PHP profile obtained using powdered POE shows high molecular weight product material eluting at about 10.3 minutes, with a mass of 15,548,068. In contrast, the profile of PHP obtained from filtered POE/ethanol shows no peak in this region, even at the high-sensitivity scale of the profile, indicating the substantial reduced presence of these high molecular weight materials in PHP obtained with dissolved aPEG starting materials.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of preparing a PEGylated hemoglobin solution that is substantially free of contaminants comprising:
   (a) dissolving an activated polyethylene glycol (aPEG) in a solvent suitable for addition to a hemoglobin solution and in which said aPEG is stabile;
   (b) filtering said dissolved aPEG through at least one filter which substantially reduces the levels of contaminants in the resulting filtered aPEG solution; and
   (c) combining said resulting filtered aPEG solution of step (b) with a hemoglobin solution.

2. The method of claim 1, wherein the aPEG is polyoxyethylene (POE).

3. The method of claim 3, wherein the solvent is ethanol.

4. The method of claim 3, wherein said at least one filter substantially reduces endotoxin contaminant levels in the filtered aPEG solution.

5. The method of claim 4, wherein said at least one filter reduces endotoxin contaminant levels in the filtered aPEG solution by at least 500 EU/cm$^2$ of filter area.

6. The method of claim 5, wherein said at least one filter comprises a 0.2 micron nylon filter.

7. The method of claim 6, wherein the hemoglobin solution comprises pyridoxylated stroma-free hemoglobin.

8. The method of claim 7, wherein said filtering and said combining are aseptically joined.

* * * * *

UNITED STATES PATENT AND TRADEMARK OFFICE
CERTIFICATE OF CORRECTION

| | | |
|---|---|---|
| PATENT NO. | : 7,038,016 B2 | Page 1 of 1 |
| APPLICATION NO. | : 09/934300 | |
| DATED | : May 2, 2006 | |
| INVENTOR(S) | : Talarico et al. | |

It is certified that error appears in the above-identified patent and that said Letters Patent is hereby corrected as shown below:

<u>Column 9</u>:

Line 14, "100,7" should read --100.7--;

<u>Column 12</u>:

Line 31, "of claim 3" should read --of claim 2--.

Signed and Sealed this

Fifth Day of September, 2006

JON W. DUDAS
*Director of the United States Patent and Trademark Office*